(12) United States Patent
Duval et al.

(10) Patent No.: US 11,890,085 B2
(45) Date of Patent: *Feb. 6, 2024

(54) IMPLANTABLE MEDICAL SENSORS AND RELATED METHODS OF USE

(71) Applicant: Boston Scientific Scimed, Inc., Maple Grove, MN (US)

(72) Inventors: George W. Duval, Sudbury, MA (US); Paul J. Smith, Smithfield, RI (US); Michael Y. Ko, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 447 days.

This patent is subject to a terminal disclaimer.

(21) Appl. No.: 17/113,537

(22) Filed: Dec. 7, 2020

(65) Prior Publication Data

US 2021/0085210 A1 Mar. 25, 2021

Related U.S. Application Data

(63) Continuation of application No. 16/209,149, filed on Dec. 4, 2018, now Pat. No. 10,881,320.

(Continued)

(51) Int. Cl.
*A61B 5/00* (2006.01)
*A61B 5/0538* (2021.01)
(Continued)

(52) U.S. Cl.
CPC ............ *A61B 5/0538* (2013.01); *A61B 5/073* (2013.01); *A61B 5/076* (2013.01); *A61B 5/14539* (2013.01); *A61B 5/4205* (2013.01); *A61B 5/4211* (2013.01); *A61B 5/4233* (2013.01); *A61B 5/687* (2013.01); *A61B 5/6861* (2013.01); *A61B 5/6871* (2013.01); *A61B 5/0031* (2013.01); *A61B 5/037* (2013.01); *A61B 5/4216* (2013.01); *A61B 5/4238* (2013.01); *A61B 5/686* (2013.01); *A61B 5/7225* (2013.01)

(58) Field of Classification Search
CPC ..... A61B 5/0031; A61B 5/037; A61B 5/0538; A61B 5/073; A61B 5/076; A61B 5/14539; A61B 5/4205; A61B 5/4211; A61B 5/4216; A61B 5/4233; A61B 5/4238; A61B 5/686; A61B 5/6861; A61B 5/687; A61B 5/6871; A61B 5/7225
See application file for complete search history.

(56) References Cited

U.S. PATENT DOCUMENTS

| 6,053,873 A * | 4/2000 | Govari ................ A61B 5/0031 600/468 |
| 8,447,404 B2 | 5/2013 | Sharma et al. |

(Continued)

*Primary Examiner* — George Manuel
(74) *Attorney, Agent, or Firm* — Bookoff McAndrews, PLLC

(57) ABSTRACT

According to one aspect, an implantable medical device may include an anchor assembly configured to anchor the medical device to a body lumen. The implantable medical device may also include a capsule. The capsule may include a pH sensor. The pH sensor may be configured to measure a pH of contents within the body lumen. The capsule may also include a power source, a controller, and an impedance sensor. The impedance sensor may be configured to measure an impedance within the body lumen.

11 Claims, 2 Drawing Sheets

Related U.S. Application Data

(60) Provisional application No. 62/594,705, filed on Dec. 5, 2017.

(51) Int. Cl.
*A61B 5/07* (2006.01)
*A61B 5/145* (2006.01)
*A61B 5/03* (2006.01)

(56) References Cited

U.S. PATENT DOCUMENTS

| | | |
|---|---|---|
| 8,831,729 B2 | 9/2014 | Policker et al. |
| 2009/0264951 A1* | 10/2009 | Sharma ............... A61N 1/0502 607/40 |
| 2011/0295335 A1 | 12/2011 | Sharma et al. |

* cited by examiner

IMPLANTABLE MEDICAL SENSORS AND RELATED METHODS OF USE

CROSS-REFERENCE TO RELATED APPLICATIONS

This is a request for filing a continuation application under 37 CFR § 1.53(b) of pending prior U.S. Nonprovisional patent application Ser. No. 16/209,149, filed on Dec. 4, 2018, which claims the benefit of priority from U.S. Provisional Application No. 62/594,705, filed on Dec. 5, 2017, each of which is incorporated herein by reference in its entirety.

TECHNICAL FIELD

Implementations of the present disclosure relate to devices and methods for measuring one or more of pH, position, and impedance with an implantable medical device. More specifically, at least some embodiments of the present disclosure relate to devices and methods for diagnosing gastroesophageal reflux disease (GERD) or other abnormalities or ailments in the gastrointestinal tract.

BACKGROUND

GERD is a condition associated with the gastrointestinal tract system. GERD is a condition in which stomach contents leak backwards from the stomach into the esophagus through the lower esophageal sphincter (LES). The leak may be caused by a weak LES or excess gastric pressure. The leaked contents may irritate the esophagus. The irritation may cause heartburn and other symptoms.

Devices for GERD diagnosis should be able to differentiate between digestion events like swallowing, stomach contraction, and vomiting. However, current GERD diagnosis devices may be imprecise in the way they differentiate between digestion events. As such, the devices may not operate in the manner desired when a digestion event takes place. Furthermore, current systems to diagnose GERD are limited in the number of sensors included, the accuracy of the system, and the limited monitoring time in which the system is effective.

Currently, pH probes are used as a standard diagnostic tool to detect GERD, however most pH probes don't have sensors that indicate directionality of the reflux event, which may result in false negative diagnoses. Also, implantable wireless pH monitoring to diagnose GERD is currently susceptible to false negative results.

The medical devices and methods described herein are provided to rectify deficiencies described in conventional diagnostic sensors and offer improvements that may help address other problems.

SUMMARY

Embodiments of the present disclosure relate to, among other things, medical devices for measuring pH, impedance, and/or position of a patient. Each of the embodiments disclosed herein may include one or more of the features described in connection with any of the other disclosed embodiments.

According to one aspect, an implantable medical device may include an anchor assembly configured to anchor the medical device to a body lumen. The implantable medical device may also include a capsule. The capsule may include a pH sensor. The pH sensor may be configured to measure a pH of contents within the body lumen. The capsule may also include a power source, a controller, and an impedance sensor. The impedance sensor may be configured to measure an impedance within the body lumen.

In other aspects of the present disclosure, the implantable medical device may include one or more of the features below. The anchor assembly may be configured to release from a wall of a body lumen within 1-7 days. The anchor assembly may be configured to couple the medical device to a wall of an esophagus. The controller may include a transmitter. The transmitter may be configured to transmit a signal to a receiver located outside of the body lumen. The capsule may be an elongated cylindrical structure forming a helix. The impedance sensor may be configured to sense a direction of travel of contents within the body lumen. The implantable medical device may be in electrical communication with a data acquisition module. The capsule may further comprise a position sensor. The anchoring assembly may include a first structure at a distal portion of the capsule and a second structure at a proximal portion of the capsule. Each of the first structure and the second structure may be configured to anchor the medical device to the body lumen. The anchoring assembly may include a bioabsorbable portion. The implantable medical device may include an optical assembly configured to visualize an area within the body lumen.

In other aspects, a method for sensing within a body lumen of a patient may include sensing a pH with an implanted medical device coupled to the body lumen. The method may also include sensing a direction of travel of contents within the body lumen with an impedance sensor of the medical device. The method may also include determining, based on the sensed pH and the sensed direction of travel, whether the patient has experienced an event. The method may further include transmitting data from the implanted medical device to a data acquisition module located outside of the body of the patient.

In other aspects of the present disclosure, the method for sensing within a body lumen of a patient may further include one or more of the features below. The method may include sensing a position of a medical device within the body lumen. The method may also include wirelessly transmitting a sensed pH and a sensed direction of travel to a data acquisition module. The method may include determining whether the sensed pH is less than 4 when determining whether the patient has experienced an event. The method may include releasing the medical device from the body lumen after a period of 1-7 days. Also, the method may include determining whether the sensed direction of travel of contents is upstream when determining whether the patient has experienced an event.

In other aspects of the present disclosure, a method for sensing within a body lumen of a patient may include sensing a direction of travel of contents within the body lumen with an impedance sensor of the medical device. The impedance sensor may be exposed to an interior of the body lumen. The method may also include determining whether the patient has experienced an event based on the sensed direction of travel. The method may further include transmitting data from the implanted medical device to a data acquisition module located outside of a body of the patient when an upstream direction of travel is sensed.

In other aspects of the present disclosure, the method for sensing within a body lumen of a patient may further include one or more of the features below. The method may also include sensing a position of the patient with the implanted medical device, and then determining whether a patient has experienced an event is further based on the sensed position. Also, the method may include releasing the implanted medical device from a wall of the body lumen after 2-7 days.

The foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient. The term "downstream" refers to the direction of flow of a substance through the gastrointestinal tract when ingested through the mouth of a patient running from the mouth through the esophagus to the stomach. The term "upstream" refers to the direction of flow of a substance from the stomach through the esophagus towards the mouth of a patient. The term "reflux event" includes a digestive event in which stomach contents or other substances leak backwards from the stomach, in an upstream direction, into the esophagus through the lower esophageal sphincter (LES). When used herein, the terms "approximately" and "substantially" may indicate a range of values within +/−5% of a stated value.

The present disclosure is drawn to implantable medical devices for measuring one or more of pH, impedance, position, and other parameters of a patient's body, and related methods. In general, embodiments of the medical devices may include a pH sensor, a position sensor, and an impedance sensor. The medical devices may be implantable into a body lumen of a patient, such as the esophagus. In some examples, the medical devices may include an attachment means for attaching the medical device to the esophageal wall.

In exemplary embodiments of the present disclosure, GERD diagnosis and treatment may be performed using a medical device including one or more sensors or sensor assemblies, a controller, and a data acquisition module. The diagnosis is initiated by implanting the medical device into a patient and monitoring one or more locations along the esophagus using the one or more sensors. The sensors generate input signals indicative of sensed pH, impedance, position, or other suitable parameters, at the location of the medical device. The controller receives the input signals and executes one or more algorithms used to determine whether the input signals are indicative of one or more digestive events. A digestive event may be a reflux event, a patient swallowing food or drink, or other digestive activity within the gastrointestinal tract. Based on the determination, the controller may transmit sensor data to one or more data acquisition modules. Though this description describes diagnostic devices for GERD, embodiments of the present disclosure may diagnose and/or treat other ailments throughout the body.

Figure 1:
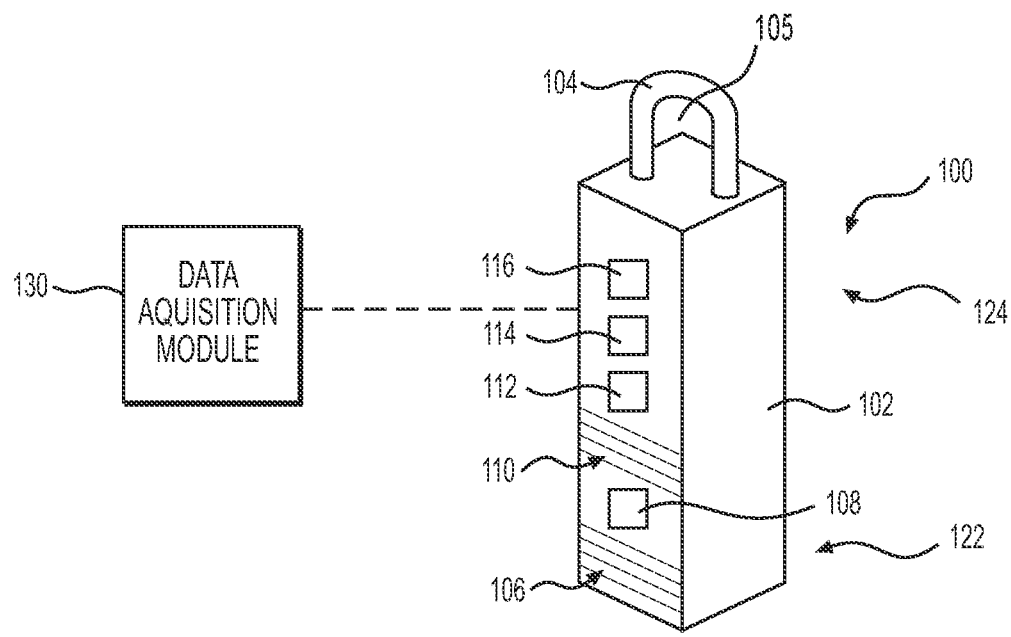
FIG. 1 illustrates a perspective view of a medical device according to aspects of the present disclosure.

Referring to FIG. 1, a medical device 100 may include a proximal anchor 104 and a distal capsule 102. Capsule 102 may have a rectangular shape and may have a distal section 122 and a proximal section 124. Anchor 104 may be coupled to the proximal section 124 of the capsule 102. As explained in further detail below, one or more sensors may be coupled to capsule 102 for measuring pH, impedance, position, posture, fluid or other substance flow, or other parameters. Capsule 102 may include at least one pH sensor 108 and may include at least two impedance sensors 106, 110. In other examples, capsule 102 may include two, three, four, or more pH sensors 108 and/or may include one, three, four, or more impedance sensors 106, 110. In some examples, a pH sensor 108 may be positioned on the capsule 102 between two impedance sensors 106, 108, one impedance sensor 106 located distal to the pH sensor 108 and one impedance sensor 110 located proximal to the pH sensor 108 (shown in FIG. 1). Capsule 102 may further include a position sensor 112, a power source 114, and a controller 116. In some examples, capsule 102 may include a plurality of motion sensors 112, power sources 114, and/or controllers 116. Capsule 102 may be wirelessly connected to a data acquisition module 130, for example, wirelessly connected via a transmitter included in controller 116 present on or in capsule 102. In other examples, a transmitter may be included in capsule 102 separate from controller 116. In some examples, capsule 102 or anchor 104 may include an optical sensor, such as a camera. A camera may be used to assist in the placement of medical device 100 within a body lumen of a patient.

Capsule 102 may be any structure that can retain the desired sensors and electrical components in the desired part of the anatomy. Capsule 102 may be spherical, pyramidal, cylindrical, or any other shape. In some examples, capsule 102 may be adapted to be received within a working channel of a delivery device, such as an endoscope or catheter. Capsule 102 may provide a protective body covering one or more components (such as battery, controller) and provide a fluid-tight seal preventing ingress of fluids that could harm operation of medical device 100. Capsule 102 may be rigid or flexible, and may be made of any suitable biocompatible material. In some examples, capsule 102 may be part of a self-powered micro-fuel cell. Capsule 102 may be made of a material that would enable bio-fuel cell production, such as a thin film metal layer or nano-carbon material. In some examples, capsule 102 or portions of capsule 102 may be a material to enable capacitive coupling, such as a thin film or non-carbon material. In some examples, capsule 102 may be a flexible cylinder with a diameter less than or equal to 5 mm, including for example 4.2 mm. Capsule 102 may be designed to be implanted approximately 3-5 cm above the lower esophageal sphincter (LES). In some examples, medical device 100 may include multiple capsules each containing separate components, such as a capsule for the pH sensor, a capsule for the control, etc.

Anchor 104 may be releasably coupled to capsule 102 and may have a shape of a loop, or partial loop, enclosing an opening 105. Anchor 104 may be an anchor assembly and may include multiple components, such as a wire loop coupled to capsule 102 and a fastening means used to couple the wire loop to a patient, such as to the esophageal wall of a patient. In some examples, anchor 104 may include a suture, a clip, a hook, an adhesive, a spike, a spiral wire, a spring, and/or a looped wire. Portions of anchor 4 may have different diameters than other portions. For example, a proximal portion of anchor 4 may have a larger diameter than a distal portion of anchor 4. In some examples, multiple anchors 104 may be coupled to different portions of capsule 102 and may be spaced apart from each other. In one example, a loop (e.g. of wire) may be coupled to a proximal section 124 of capsule 102 and a second loop may be coupled to a distal section 122 of capsule 102. In some examples, anchor 104 may encase capsule 102. The use of multiple anchors coupled to capsule 102, which may provide multiple anchoring points affixing the capsule 102 to the esophageal wall or other body lumen, may assist in maintaining directional orientation of the medical device 100 within a body lumen of the patient.

Anchor 104 may include an actuator for releasing the capsule 102 from all or part of the anchor 104. In some examples, anchor 104 may include a grasper or clipping device, or may include an adhesive present on a portion of the surface area of capsule 102. In other examples, anchor 104 may include a lever, button, slide, or switch, to provide a mechanical, magnetic, and/or electrical release mechanism to release the capsule 102 from the anchor 104, a portion of the anchor 104 or a portion of the anchor assembly. Releasing the capsule 102 from the anchor 104 may allow the capsule 102 to pass through the gastrointestinal tract of the patient to exit the patient's body. In some examples, anchor 104 or a portion of anchor may be a bioabsorbable structure which may deteriorate over a predetermined period of time, such as one, two, three, four, five, six, or seven days, two weeks, one month, or any other time period. For example, bioabsorbable suture may be used to tie anchor 104 in FIG. 1, to the esophageal wall. The suture may absorb over a predetermined time, releasing anchor 104 from the wall, allowing capsule 102 to travel through the digestive tract. In other examples, a bioadhesive present on a portion of the surface area of capsule may be configured to deteriorate and release capsule after a specific period of time.

Once implanted in a patient, anchor 104 may be secured to a portion of the esophageal wall to help secure medical device 100. As described further below, anchor 104 may be positioned in the esophagus or the gastro-esophageal junction (GEJ) region. In some examples, medical device 100 does not include anchor 104. In some other examples, medical device 100 may exert a radially outward force on a body lumen to secure medical device 100 to the inner wall of a body lumen for example, capsule may be ring-shaped with its radial outer surface contacting the interior surface of the esophageal wall. The ring-shaped capsule may be sufficiently rigid and have a sufficient diameter to anchor itself in the esophageal lumen. The ring-shaped capsule may be sufficiently rigid In other examples, medical device 100 may be secured directly to the patient's tissue using sutures or any other suitable attachment mechanism. In some examples, medical device 100 may have a long geometry whereas the device length exceeds the diameter of the body lumen in which it is implanted. In some examples, medical device 100 may include an elongated capsule and a plurality of impedance and pH sensors inside the elongated capsule, and may have a length (long dimension) greater than the actual width or diameter of the body lumen in which the medical device is inserted.

pH sensor 108 may be used to monitor pH values of bodily fluids, including stomach fluids, and other substances within the body of the patient. pH sensor 108 is coupled to capsule 102 so that sensor 108 comes into contact with the bodily fluid to be monitored. In some examples, pH sensor may be partially or fully exposed to contents within the gastrointestinal tract. pH monitoring using pH sensor 108 may be performed continuously, intermittently, or upon the trigger of another sensory input detector from another sensor included in or on capsule 102, such as position sensor 112 or impedance sensor 106, 110. In some examples, pH sensor 108 may include one or more sensors forming a pH sensor assembly. pH sensor 108 may be in electrical communication with any of the other components included in medical device 100, including data acquisition module 130 or any other sensors incorporated in medical device 100.

Position sensor 112 may detect the position of the patient and/or the position of the esophagus relative to the ground. Position sensor 112 may include a posture sensor, an accelerometer, a gyroscopic sensor, a 6-axis motion sensing device, a digital position sensor, or any combination thereof. Position sensor 112 may detect whether the patient is standing or sitting upright, with the patients esophagus running substantially perpendicular to the ground, or lying down, with the patient's esophagus running substantially parallel to the ground. In some examples, position sensor 112 may detect the position of capsule 102 relative to the esophagus or other internal body lumen of the patient. Position sensor 112 may be in electrical communication with any of the other components included in medical device 100, including data acquisition module 130 or any other sensors incorporated in medical device 100.

Impedance sensors 106, 110 may be multichannel intraluminal impedance (MII) sensors or any other impedance sensors suitable to detect an impedance value therebetween and suitable for implantation in a human body. Impedance sensors 106, 110 may detect the intraesophageal bolus transport or directional flow activity within a body lumen of the patient. In some examples, impedance sensors 106, 110 may measure an impedance value between each sensor 106, 110, or an impedance delta. In some examples, medical device 100 may include one impedance sensor, or three or more impedance sensors. When medical device 100 is implanted into a body lumen of a patient, impedance sensors 106, 110 may detect when the body lumen is filled with a substance, such as a gas, liquid, or solid, and which direction the substance is flowing through the body lumen, such as downstream or upstream. Impedance sensors 106, 110 may distinguish between substances being swallowed by the patient and a reflux event associated with GERD. Impedance sensors 106, 110 may be positioned on or in capsule 102, and capsule 102 may be coupled to the esophageal wall of a patient in such a way to position impedance sensors 106, 110 along a direction of travel of substances through the esophagus, along the longitudinal axis of the esophagus. When anchoring capsule 102, impedance sensors 106, 110 may need to be positioned to expose the sensors to the interior passageway of the esophagus and may not be positioned against the esophageal wall. By detecting whether a digestive event includes substances traveling downstream or upstream the gastrointestinal system, impedance sensors 106, 110 may assist in avoiding false negative or false positive diagnostic results that may result from recording data during downstream flow activity, such as when the patient is eating food, as a reflux event associated with GERD.

The various sensors and components of medical device 100 may be connected to power source 114 to supply power to the components. Power source 114 may be a battery, such as an implantable battery or wirelessly rechargeable battery coupled to capsule 102 or anchor 104. In other examples, power source 114 may include multiple batteries or one or more batteries combined with another source of power. In some examples, power source 114 may be a self-powered device such as a Microbial Fuel Cell (MFC) with a grapheme anode, which may be powered by saliva, a kinetic energy harvesting device, and/or a battery. Power source 114 may be wirelessly charged by a device, such as a battery charging device located outside of the patient's body.

Controller 116 may include a processor that is generally configured to accept information from any of the sensors or electrical components of medical device 100, and process the information according to one or more algorithms. The processor may be a digital integrated circuit processor, analog processor or any other suitable logic or control system that carries out control algorithms. In some examples, controller 116 may be an M0-M4 class ARM device, a flexible microcontroller, and/or another form of embedded processor. Controller 116 may record treatment or diagnostic parameters, e.g., sensor data, so that the data may be accessed for concurrent or subsequent analysis. Controller 116 may include software that provides a user interface to components within the system. The software may enable a user (e.g., patient or clinician) to configure, monitor, and control operation of medical device 100. As described in further detail below, software may be configured to periodically or continuously sample the sensors present on medical device 100 and broadcast information to data acquisition module 130. In some examples, controller 116 may be configured to broadcast information only when certain events occur, such as only when the pH sensor 108 detects a pH below a certain threshold value, when impedance sensors 106, 110 detect a certain impedance, or when position sensor 112 detects a certain position or posture of the patient.

Controller 116 may include a transmitter capable of broadcasting a wireless signal to data acquisition module 130. For example, controller 116 may include an integrated radio for a transmitter such as a NORDIC nRF52. In some examples, a transmitter included in controller 116 may be a 2.4 GHz transmitter operable with Bluetooth technology and/or capable of being paired to portable devices such as a smartphone or a tablet. In other examples, a transmitter included in controller 116 may be a proprietary 433 MHz ultra high frequency (UHF) transmitter capable of being uniquely paired with a receiver, such as a smartphone or smart watch, the patient could wear.

Data Acquisition Module 130 may be any means for receiving data transmitted wirelessly from medical device 100. In some examples, data acquisition module 130 may be an application downloaded to a portable device, such as a smartphone or a tablet. In other examples, data acquisition module 130 may include software downloaded to a computer or contained within a portable electronic device worn by the patient, such as a smart watch or other wearable electronic device. Data transmitted from medical device 100 may be stored and processed by data acquisition module 130 for analysis by the patient or the patient's clinician. In some examples, data acquisition module 130 may include a user interface by which the patient can input his or her symptoms during a digestive event, such as symptoms that occur while experiencing a reflux event. For example, the patient may input into the data acquisition module 130 a symptomatic event description and record the time when the symptomatic event occurred, the patient's body position, and/or food ingested prior to the event. Data Acquisition module 130 may provide input parameters, such as a symptomatic event description and time of event occurrence, within a software application present on the patient's smartphone, tablet, computer, or other electronic device.

Figure 2:
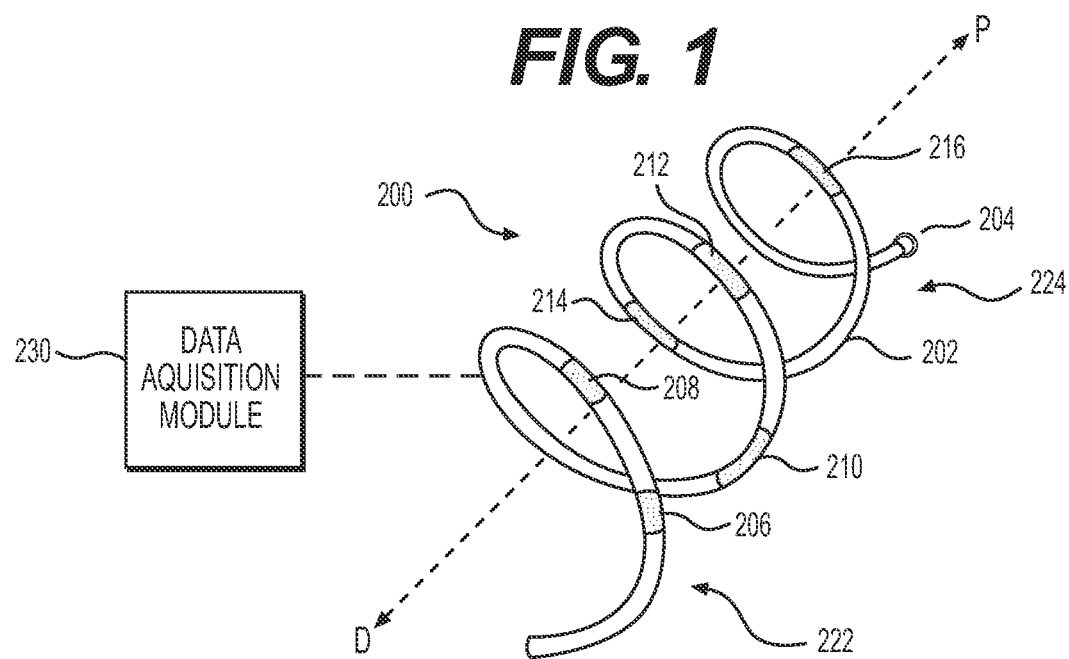
FIG. 2 illustrates a perspective view of a medical device according to aspects of the present disclosure.

FIG. 2 illustrates an additional example of a medical device 200 in accordance with the present disclosure and similar to medical device 100 discussed above. Medical device 200 includes capsule 202, anchor 204, pH sensor 208, impedance sensors 206, 210, position sensor 212, power source 214, controller 216, and data acquisition module 230. The same or similar components of medical device 100 and medical device 200 may have the same or similar characteristics as previously described in connection with medical device 100. This discussion therefore will focus on the differences between devices 100, 200. Medical device 200 has an elongated cylindrical structure forming a helix or spring shape. In some examples, medical device 200 may be designed to extend along and against the esophageal wall and may include a curvature that substantially matches with that of the esophageal wall of a patient. In other examples, medical device 200 may be flexible and/or may be biased radially outward from the P-D (proximal-distal) axis (shown in FIG. 2) such that the radially outer surface is pressed against the esophageal wall when medical device 200 is implanted in the esophagus of a patient. Capsule 202 may have a contracted delivery state and an expanded implantation state.

Another exemplary embodiment of a medical device in accordance with the present disclosure may includes a series of capsules each anchored separately within a body lumen of a patient. In such an embodiment, the same or similar components of medical device 100 and medical device 200 may be included in multiple different capsules and may have the same or similar characteristics as previously described in connection with medical device 100. For example, a cluster of capsules may be coupled to a wall of a body lumen with a pH sensor in one capsule, a impedance sensor in another capsule, a position sensor in another capsule, etc. In this cluster configuration, each capsule may be in electronic communication with each other capsule in the cluster, and all of the capsules may be in electronic communication with a data acquisition module located outside of the patient.

Medical devices disclosed herein, such as medical devices 100 and 200, may be used in a variety of contexts. In one example, medical device 100 may be used to diagnose GERD.

Medical devices disclosed herein may be delivered to a patient using standard delivery methods and devices. For example, medical device 100 may be inserted into a delivery catheter and placed transorally into the patient's gastrointestinal system. In some examples, medical device 100 may be transported to a target esophageal site within the jaws of an endoscopic clipping device. The target esophageal site may be 2-5 cm from the lower esophageal sphincter. Coupling medical device 100 to the esophageal wall (or other portion of the GI tract) may include anchoring capsule 102 with one or more anchors 104 such that the distal section 122 is downstream from the proximal section 124 of medical device 100. For example, medical device 100 may be coupled to the esophageal wall with an anchor assembly including a first anchor in the proximal section 124 of medical device 100 and a second anchor in the distal section 122 of medical device 100 such that the first anchor is upstream from the second anchor. Anchor 104, or multiple anchors if used, may be coupled to the esophageal wall of the patient to position medical device so that impedance sensors 106, 110 may detect the directional flow of substances through the esophagus.

After implantation, medical device 100 may detect digestive events, such as reflux of stomach contents, and wirelessly transmit sensor data, such as data from pH sensor 108, position sensor 112, and impedance sensors 106, 110 to data acquisition module 130. In some examples, data may be temporarily stored on medical device 100, such as in a memory of controller 116, prior to transmission to data acquisition module 130.

After collection of data using data acquisition module 130, an anchor assembly may be configured to release the medical device from a body lumen of the patient, such as the esophageal wall. The anchor assembly may be configured to release after a specific or otherwise predetermined time period. In some examples, the anchor assembly may be configured to release after one, two, three, four, five, six, or seven days, two weeks, or one month. In other examples, the implanted medical device may be removed by a clinician using standard removal methods. For example, medical device 100 may be pulled transorally from the patient.

Figure 3:
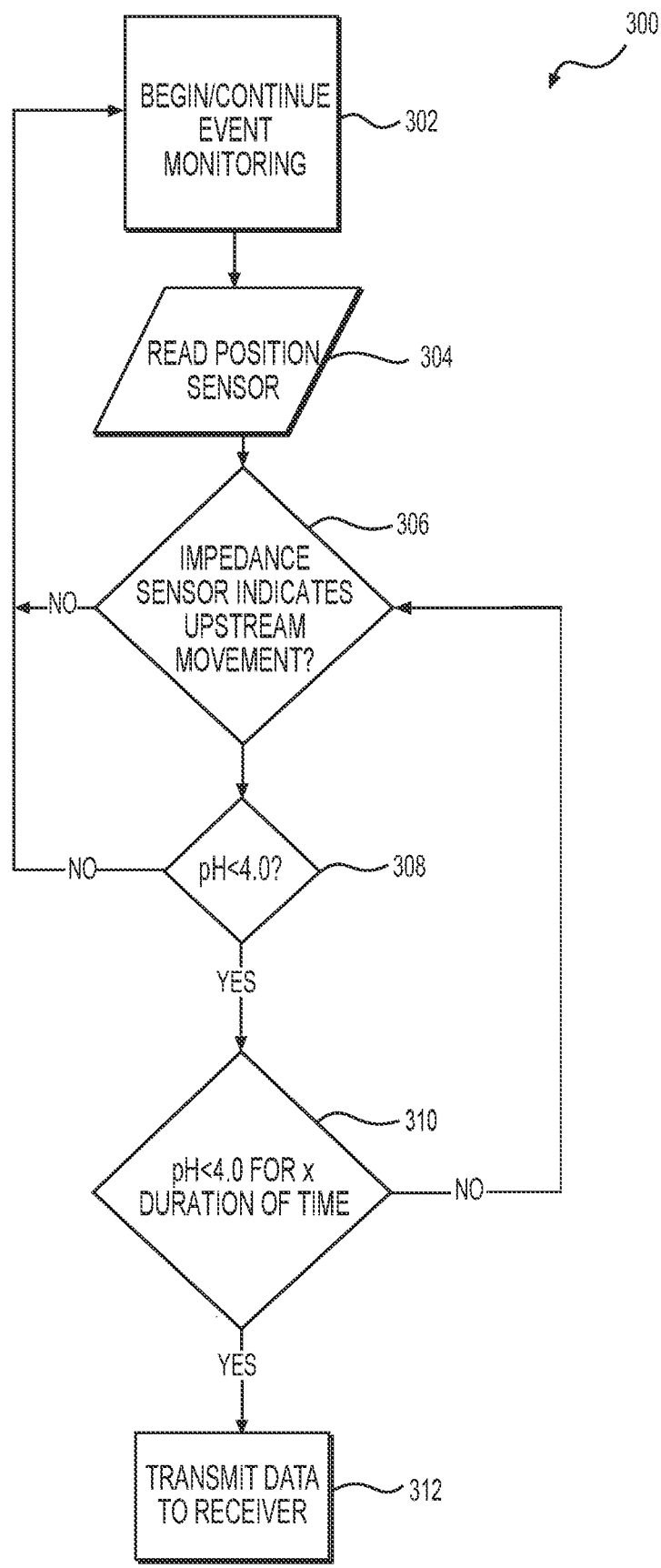
FIG. 3 illustrates a block diagram of an exemplary method of using the medical devices disclosed herein according to aspects of the present disclosure.

Controller 116 may be configured to execute specific algorithms to determine whether (or when) to transmit and/or record a digestive event. Controller 116 may be configured to aggregate sensor data from any of the sensors present on medical device 100, such as pH sensor 108, position sensor 112, and impedance sensors 106, 110. FIG. 3 illustrates an example of a "broadcast on event" monitoring algorithm 300 that may be included in controller 116 and may require specific sensor data values to transmit digestive event data to data acquisition module 130. "Broadcast on event" may mean controller 116 is configured to transmit data to data acquisition module 130 when certain sensor data value thresholds are met or exceeded.

In FIG. 3, step 302 includes beginning digestive event monitoring, which may be initiated at the time medical device 100 is implanted into a patient, such as by manually pressing a button or powering on the device, or may be initiated after implantation, such as wirelessly initiated using data acquisition module 130. Step 304 includes reading position sensor data to determine the posture of the patient, e.g. whether the patient is upright or lying down. In step 306, algorithm 300 determines whether impedance sensors 106, 110 indicate upstream movement of a substance flowing through the esophagus, which would indicate a reflux event is occurring. For example, impedance sensors 106, 110 may determine an impedance delta between two impedance sensors that may indicate a particular direction of substance movement through the esophagus. By reading an impedance delta from the impedance sensors 106, 110, the controller 116 may determine whether the digestive event includes substances traveling upstream or downstream the esophagus. If, after step 306, data from the impedance sensors 106, 110 indicates a substance is moving downstream in the esophagus, controller 116 may return to step 302 to continue event monitoring, without recording the event since downstream movement most likely indicates the patient is eating or drinking and not having a reflux event. If, after step 306, data from the impedance sensors 106, 110 indicates a substance is moving upstream in the esophagus, then the controller 116 may proceed to step 308 and may collect a pH sensor's data and/or determine whether an adaptive threshold has been met.

While FIG. 3 indicates that only sensor data with a pH of less than 4 will move to step 310 of algorithm 300, the pH threshold level to move to step 310 may be any adaptive threshold. The adaptive threshold may be set and periodically changed by a patient's doctor, may be stored on the device, and may depend on the level of severity of the patient's illness. The adaptive threshold may be set based on the existence and/or severity of the patient's GERD or other conditions such as Non-erosive Reflux Disease (NERD), hypersensitive esophagus, whether the patient is receiving proton pump inhibitors (PPIs), among others. In some examples, the adaptive threshold may be set to a threshold pH of 4 or less (as shown in step 310 of FIG. 3) when a patient has mild to moderate GERD, for example when the patient has a Los Angeles GERD Grade Classification of A or B. In other examples, the adaptive threshold may be set to a threshold pH of 6 or less when a patient has moderate to severe GERD, for example when the patient has a Los Angeles GERD Grade Classification of C or D. In other examples, the adaptive threshold may be set to a threshold pH of 5 or less when a patient has NERD, hypersensitive esophagus, whether the patient is receiving PPIs, or has other related conditions.

If the medical device 100 determines the adaptive threshold has not been met, shown in FIG. 3 as determining the pH level is not below 4, then the algorithm 300 may record the event as a non-acidic reflux event and move back to step 302 to continue event monitoring. If the device 100 determines the adaptive threshold is met or exceeded in step 308 (shown in FIG. 3 as determining whether the pH reading from the pH sensor 108 is lower than 4), algorithm 300 will move to step 310 and monitor the data from the sensors for a duration of time X, where X may be a monitoring time and may be any period of time such as 5 seconds. The patient's doctor may set the monitoring time X for step 310 and the time may be 1, 2, 3, 4, 5, 6, 7, 10, or 15 seconds, or any other amount of time. In step 310, if the adaptive threshold (shown in FIG. 3 as ph<4 in step 310) is met or exceeded for the entire monitoring time X, the algorithm 300 may proceed to step 312 and transmit to a receiver (such as data acquisition module 130, 230) an alert of a GERD event. If the adaptive threshold is not met or exceeded for the entire monitoring time X in step 310, algorithm 300 my record a "peak detection only" event and proceed to step 306 of determining whether the impedance sensor indicates upstream movement. In some examples, if the adaptive threshold is not met or exceeded for the entire monitoring time X in step 310, algorithm 300 may move back to step 302 and continue event monitoring.

After transmission of data received by the sensors of the medical device to a receiver, such as in step 312 of algorithm 300, the controller 116 may return to step 302 and continue digestion event monitoring. Algorithm 300 is an exemplary algorithm, and any sensor threshold value requirements and/or adaptive threshold value requirements may be added or interchanged with the requirements of algorithm 300.

By utilizing an algorithm such as algorithm 300 to determine when to record digestive events while testing a patient for GERD, the frequency of false positive and false negative testing may be mitigated. For example, by utilizing multiple different sensors for position, pH, and impedance in an implantable device to collect patient data over a longer period of time than conventional diagnostic medical devices, clinicians may have more accurate and reliable diagnosis of GERD in patients. Similarly, utilizing a monitoring time, such as step 310 in algorithm 300, may mitigate the number of false positive reflux events detected by the sensors. Algorithm 300 utilized in the medical devices discuss herein above provides a means to filter digestive events and only record events that include sensor data aligning with a reflux event.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method for sensing within a body lumen of a patient, comprising:
    sensing a pH with an implanted medical device coupled to the body lumen or sensing a direction of travel of contents within the body lumen with an impedance sensor of the medical device;
    based on the sensed pH or the sensed direction of travel, determining whether the patient has experienced an event;
    transmitting data from the implanted medical device to a data acquisition module located outside of a body of the patient; and
    releasing the medical device from a wall of the body lumen via deterioration of a bioabsorbable portion of the medical device.

2. The method of claim 1, further comprising sensing a position of the medical device within the body lumen.

3. The method of claim 1, further comprising wirelessly transmitting the sensed pH and the sensed direction of travel to the data acquisition module.

4. The method of claim 1, wherein determining whether the patient has experienced an event includes determining whether the sensed pH is less than 4 for a period of 5 or more seconds.

5. The method of claim 1, wherein the bioabsorbable portion of the medical device is configured to deteriorate after a period of 1-7 days.

6. The method of claim 1, wherein determining whether the patient has experienced an event includes determining whether the sensed direction of travel of contents is upstream.

7. The method of claim 1, wherein the implanted medical device is in the shape of a helix.

8. The method of claim 1, further comprising visualizing an area within the patient using an optical assembly of the implanted medical device.

9. The method of claim 1, wherein the body lumen is the patient's esophagus.

10. The method of claim 1, wherein sensing a pH or sensing a direction of travel of contents includes sensing a pH with an implanted medical device coupled to the body lumen.

11. The method of claim 1, wherein sensing a pH or sensing a direction of travel of contents includes sensing a direction of travel of contents within the body lumen with an impedance sensor of the medical device.

* * * * *